United States Patent [19]

Smith

[11] 4,039,521

[45] Aug. 2, 1977

[54] AROMATIC DIAZONIUM BIS(FLUORINATED ALKYLSULFONYL) METHIDES

[75] Inventor: George H. Smith, Maplewood, Minn.

[73] Assignee: Minnesota Mining and Manufacturing Company, St. Paul, Minn.

[21] Appl. No.: 353,297

[22] Filed: Apr. 23, 1973

[51] Int. Cl.[2] ...................... C07C 113/04; B01J 31/02; G03C 1/52

[52] U.S. Cl. .................................. 260/141; 96/91 R; 252/426

[58] Field of Search .......................................... 260/141

[56] References Cited

U.S. PATENT DOCUMENTS

| | | | |
|---|---|---|---|
| 3,578,457 | 5/1971 | Houtman et al. ................ | 260/141 X |
| 3,660,372 | 5/1972 | Schoenewaldt et al. ........... | 260/141 |
| 3,666,474 | 5/1972 | Moore ............................. | 260/141 X |

FOREIGN PATENT DOCUMENTS

| | | | |
|---|---|---|---|
| 761,054 | 11/1956 | United Kingdom ................ | 260/141 |

OTHER PUBLICATIONS

Kropp et al., Chemical Abstracts, vol. 74, p. 33, Item No. 43074x (1971).
Neplyuev et al., Chemical Abstracts, vol. 73, p. 288, Item No. 21461e (1970).

*Primary Examiner*—Floyd D. Higel
*Attorney, Agent, or Firm*—Cruzan Alexander; Donald M. Sell; Mark A. Litman

[57] ABSTRACT

Light sensitive diazonium compounds having an aromatic stable light sensitive nucleus with a bis-(fluorinated alkylsulfonyl) methide anion are found to be useful for many photosensitive systems. The fluorinated sulfonyl contains a highly fluorinated alkyl moiety.

6 Claims, No Drawings

AROMATIC DIAZONIUM BIS(FLUORINATED ALKYLSULFONYL) METHIDES

Diazonium compounds have long been used in photosensitive systems. Generally, aromatic amines have been converted to diazonium compounds, as by reaction with nitrous acid in the presence of hydrochloric acid. The general type of compound used and produced by the prior art has been an aromatic nucleus, diazonium group (—N≡N+), and an anion such as halide, sulphate, sulphonate, etc. The anion has a minor role in stabilizing the diazonium compound to thermal shock and in influencing the light sensitivity of the compounds.

It is an aspect of this invention to extend the functional utility of diazonium compounds as they are known in the art by providing the diazonium compound with a carbanion which will not adversely affect the light-sensitive characteristics of the diazonium compounds. It is a further object of the invention to add new carbanions to aromatic diazonium nuclei which will broaden the utility of aromatic diazonium compounds.

It is another aspect of this invention to provide aromatic, stable, light-sensitive diazonium nuclei with carbanions having utility for photosensitive systems.

In accordance with this invention, stable diazonium aromatic, light-sensitive nuclei are associated with bis(-fluorinated alkylsulfonyl) methide anions. This term also includes bis(fluorinated alkylsulfonyl) alkyl methides.

There are many known diazonium cationic nuclei. The nuclei may be represented by the general formula:

$$ArN_2^+$$

wherein $N_2$ is the diazonium group (-N≡N+) and Ar represents those aromatic nuclei known in the art as useful in forming light-sensitive diazonium compounds. Such aromatic nuclei are well known and recognized in the art, as for example shown by Kosar, *Light-Sensitive Systems,* John Wiley and Sons, Inc., New York, N.Y., 1965, pp. 202–214, and by Glafkides, *Photographic Chemistry,* Vol. II, Fountain Press, London, 1960, pp. 709–725. The disclosure of these references relating to diazonium compounds is incorporated herein. The cationic portion of the diazonium compounds of this invention may include any of the aromatic, light-sensitive cationic diazonium nuclei known in the art.

The aromatic portion of the molecule has played the major role in the utility of diazonium salts. The hundreds of structural variations in this portion of the molecule have been made to alter light sensitivity, thermal-shock stability and color coupling reactions. The anion has always played the minor role in affecting the properties of the salts and the utilization of the diazonium salts in light sensitive systems.

To this class of aromatic radicals which constitutes the art-recognized class of stable, light-sensitive diazonium nuclei is added a carbanion which is a bis(-fluorinated alkylsulfonyl) methide.

The compounds of this invention may therefore be represented by the general formula:

$$ArN_2{+}CR(SO_2R_f)_2^-$$

wherein $ArN_2^+$ is a stable, aromatic, light-sensitive diazonium nucleus, $R_f$ is a substantially fluorinated alkyl group, and R is a lower alkyl group ($C_1$ to $C_6$) or a hydrogen atom. The $R_f$ groups in the salt need not be identical and may vary independently of one another. By stable nucleus, it is meant that the diazonium compound with that nucleus will not autodegenerate at a temperature of less than about 4° C. The most preferred aromatic nuclei are residues of diazo-p-aminobenzenes and their aldehyde condensation products.

The fluorinated alkyl group may be straight-chain, branch-chain, or cyclic, and may have any length carbon chain, although conventionally a twenty carbon atom limit for the fluorinated alkyl group is preferred. The more preferred range is from one to eight carbon atoms.

With the use of a $C_1$ or $C_2$ group in the fluorinated alkyl sulfonyl group, the $C_1$ or $C_2$ group should be perfluoroalkyl. With a $C_3$ alkyl group there may be up to two atoms of another normally gaseous halogen, i.e., chlorine and/or bromine. With $C_4$ and higher there may be up to about two or three atoms of terminal chlorine, bromine and/or hydrogen in the fluorinated alkyl group. This description of the useful fluorinated alkyls for the invention defines the term "substantially fluorinated alkyls" as used in the practice of this invention.

This carbanion may be characterized by reference to its corresponding parent sulfones which generally have a pKa of less than or equal to about 3.0. It is believed that all such bis(fluorinated alkylsulfonyl) methide carbanions having such a pKa will be desirable, although with carbanions of greater size, higher pKa's can be tolerated. This characterization of the group is a narrower description of the requirements for the carbanion in that the strength of the carbanion is a factor in the stabilization of the diazonium nuclei. Sulfones having a pKa of less than 3.0 include bis(perfluoroalkylsulfonyl) and bis(perfluoroalkylsulfonyl) partially substituted with chlorine, bromine and/or hydrogen.

The photolysis of diazonium compounds has been the subject of many studies. It is known that the photolysis products vary with the environment present during their decomposition. It appears that there are several products of photolysis of the compounds of the present invention: one from the aromatic diazonium cation $ArN_2^+$ and another from the bis(fluorinated alkylsulfonyl) methide carbanion $CR(SO_2R_f)_2^-$. The photolysis product from the bis(fluorinated alkylsulfonyl) methide carbanion has been found to be useful as a polymerization catalyst, as a dye coupler, and as an acid catalyst for various reactions. Therefore, the compounds of this invention can be used in photopolymerizable polymeric compositions as the photosensitive material therein which will initiate the polymerization.

A preferred general method for forming the light-sensitive diazonium compounds of this invention may be expressed as follows:

$$ArN_2^+X^- + M^+CR(SO_2R_f)_2^- \rightarrow ArN_2^+CR(SO_2R_f)_2^- + M^+X^-$$

wherein X is an inorganic anion and M is a metallic cation.

Specific examples of how compounds of this invention may be produced by the foregoing method are as follows:

EXAMPLE I 2.3 grams (0.01 M) of p-anilinobenzenediazonium chloride were dissolved in 35 ml. of water. 3.2 grams (0.01 M) of potassium bis-(trifluoromethylsulfonyl) methide were dissolved in 40 ml. of water. To the solution of the potassium substituted methide was added a small amount of the diazonium salt solution with stirring until an oil precipitated. Stirring was continued until the oil solidified and then the remaining potassium salt solution was slowly added with continued stirring. The yellow solid product was filtered to give 3.6 grams of the desired product. A crystallized sample melted at 87°–88° C and the following analytical data was obtained:

| | C | H | N | F |
|---|---|---|---|---|
| % Calculated | 37.8 | 2.3 | 8.9 | 24.0 |
| % Found | 37.5 | 2.5 | 9.1 | 24.1 |

This data confirmed the following desired structure:

$C_6H_5NHC_6H_4N_2\ ^+CH(SO_2CF_3)_2^-$ I

EXAMPLES II - V

In a similar manner, the following compounds were prepared:

II

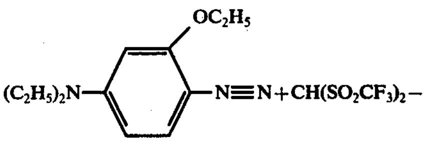

M.p. 70.5-71.5° C

III

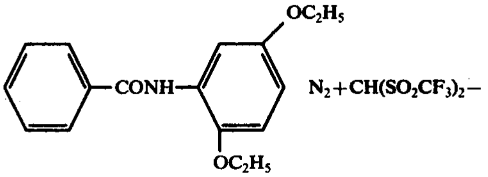

M.p. 119-121° C

IV

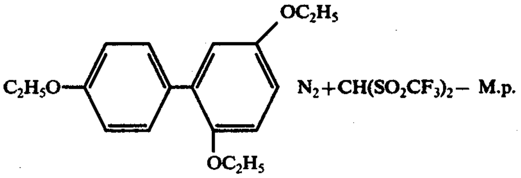

M.p. 115-117° C

V

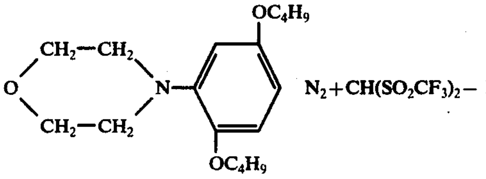

M.p. 73-75° C

EXAMPLE VI

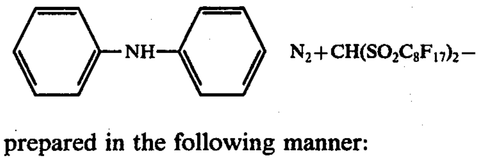

was prepared in the following manner:

0.35 grams 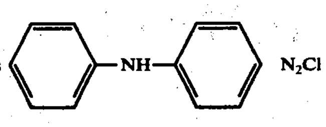

was dissolved in 3 ml. of water, 1.5 grams of potassium bis(perfluorooctylsulfonyl) methide was dispersed in 20 ml. of methanol. The aqueous solution of the diazonium chloride was added with stirring to the methide dispersion. The desired product formed as a precipitate insoluble in water. It was crystallized from aqueous methanol and was found to have a melting point of 139° - 140° C.

EXAMPLE VII

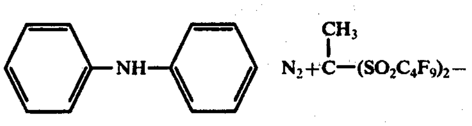

was prepared in the following manner:

3.0 grams of $CH_3CH(SO_2C_4F_9)_2$ was dispersed in 45 ml. of methanol. This was neutralized with sodium carbonate to a pH of 7.0. To this neutralized dispersion was added with stirring, a solution of 1.16 grams of

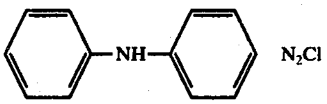

in 20 ml. of water. The precipitated product was filtered and washed with water. The yield was 2.8 grams of product which melted at 106°-107° C.

EXAMPLE VIII

Light sensitive aldehyde condensation products of p-diazo diphenylamine are well known in the art and are described in U.S. Pat. Nos. 2,714,066 and 3,085,008 and are commercially available as Diazo Resins. (Lithe A from Andrews Paper and Chem. Co.). 9.5 grams of bis(perfluorooctylsulfonyl) methane was dissolved in 1000 ml. of a 1:1 mixture of acetone and water. 90% of the stoichiometric amount of sodium hydroxide to form the mono sodium salt was added. With good stirring was then added dropwise a solution of 3.0 grams of the diazo resin dissolved in 200 ml. of water. Stirring was continued for about 20 minutes and the yellow light sensitive product precipitated after standing about 1 hour and was recovered by filtration.

EXAMPLE IX

The following solution was prepared and knife coated 3.0 mil wet on a polyester film.

10 ml 5% w/v alcohol soluble cellulose acetate butyrate in methanol 0.015 g. p-anilinobenzenediazonium bis(tri-fluoromethylsulfonyl)

A sample portion of the coated film was imagewise exposed for 10 sec. to a visible light intensity of 10,000 foot candles. The exposed sample was then heated at 115° C for 15 sec. against a receptor paper containing an acid sensitive leuco dye in a polyvinyl chloride binder. The photogenerated sulfone heat transferred to the leuco dye receptor causing formation of the dye to give an excellent negative copy of the original.

I claim:

1. A light-sensitive diazonium salt compound the cation of which is a stable, aromatic, light-sensitive nucleus and the anion of which is a bis(fluorinated alkylsulfonyl) methide, the alkyl portion of the alkylsulfonyl being substantially fluorinated.

2. The diazonium salt of claim 1 wherein the anion is a bis(perfluoroalkylsulfonyl) methide.

3. The diazonium salt of claim 1 which is represented by the formula $$ArN_2^+CR(SO_2R_f)_2^-$$

wherein $ArN_2^+$ is a stable, aromatic, light-sensitive diazonium nucleus,

R is a hydrogen atom or a lower alkyl group, and $R_f$ is a substantially fluorinated alkyl group.

4. The diazonium salt of claim 3 wherein each $R_f$ independently contains from 1 to 20 carbon atoms and is a perfluoroalkyl.

5. The diazonium salt of claim 3 wherein the diazonium nucleus is a residue of diazo-p-aminobenzene or an aldehyde condensation product of diazo-p-aminobenzene.

6. The diazonium salt of claim 5 wherein each $R_f$ is a perfluoroalkyl of from 1 to 20 carbon atoms.

* * * * *